(12) United States Patent
Ellman et al.

(10) Patent No.: US 7,226,444 B1
(45) Date of Patent: Jun. 5, 2007

(54) POSITION-CONTROLLABLE LASER SURGICAL INSTRUMENT

(76) Inventors: Alan G. Ellman, 3333 Royal Ave., Oceanside, NY (US) 11572; Jon C. Garito, 3333 Royal Ave., Oceanside, NY (US) 11572

( * ) Notice: Subject to any disclaimer, the term of this patent is extended or adjusted under 35 U.S.C. 154(b) by 242 days.

(21) Appl. No.: 10/921,247

(22) Filed: Aug. 19, 2004

(51) Int. Cl.
*A41B 18/20* (2006.01)
(52) U.S. Cl. .............................. 606/15; 606/16; 606/41
(58) Field of Classification Search ............. 606/4–17, 606/41–52
See application file for complete search history.

(56) References Cited

U.S. PATENT DOCUMENTS

| 5,469,524 | A  | * | 11/1995 | Esch et al. ................... 385/118 |
| 5,855,577 | A  | * | 1/1999 | Murphy-Chutorian et al. . 606/7 |
| 6,231,571 | B1 | * | 5/2001 | Ellman et al. ................ 606/41 |
| 7,101,370 | B2 | * | 9/2006 | Garito et al. ................. 606/41 |

* cited by examiner

*Primary Examiner*—A. Farah

(57) ABSTRACT

A disposable or reusable surgical laser handpiece having an extendable and retractable active laser fiber tip and housed in a body comprising an actuating handle for use in various surgical laser procedures. The fiber tip when extended can be given a specific configuration by associating the fiber with a shaped memory member. The housing can also be constructed to incorporate bipolar or unipolar electrosurgical electrodes.

13 Claims, 7 Drawing Sheets

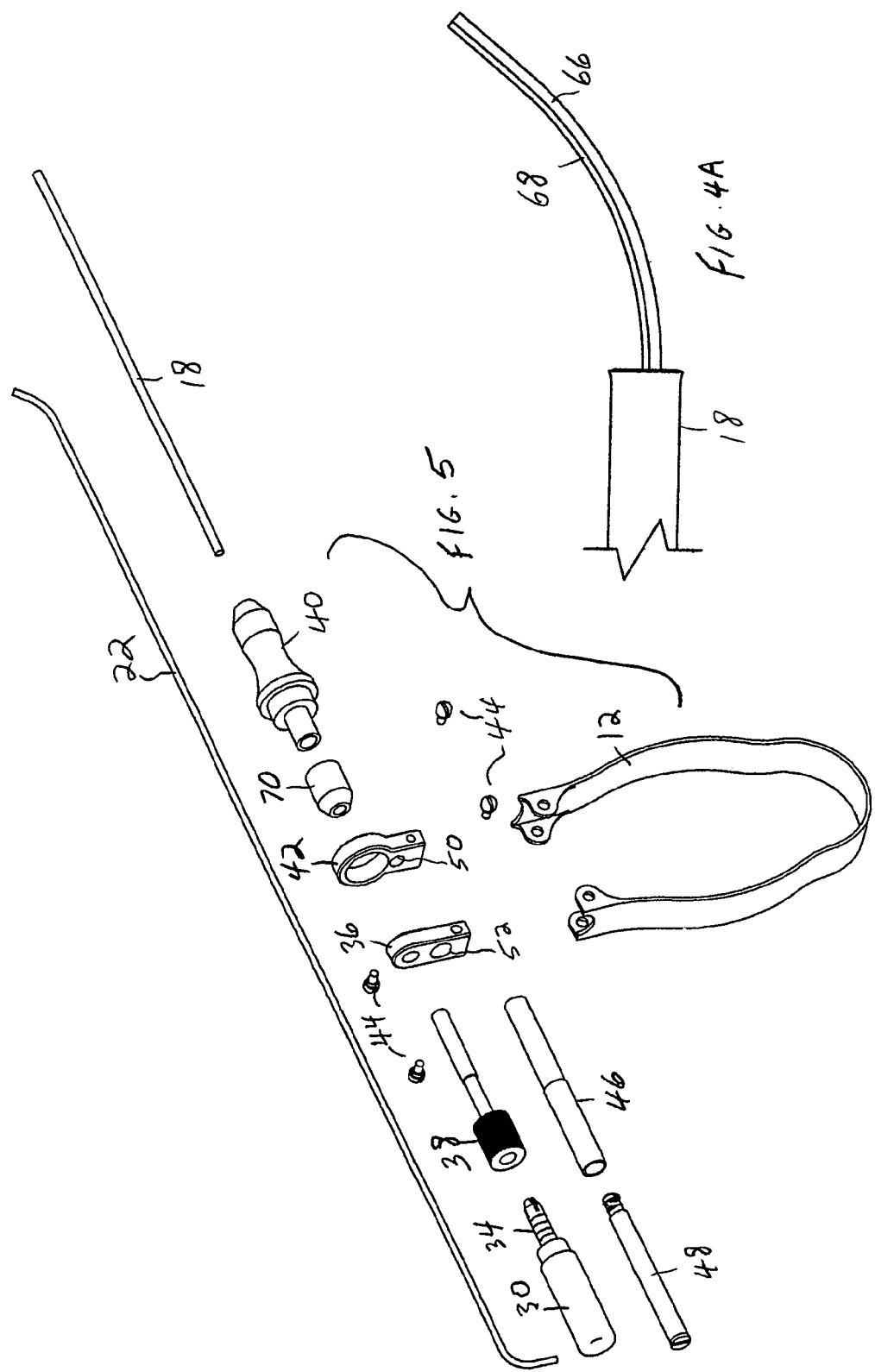

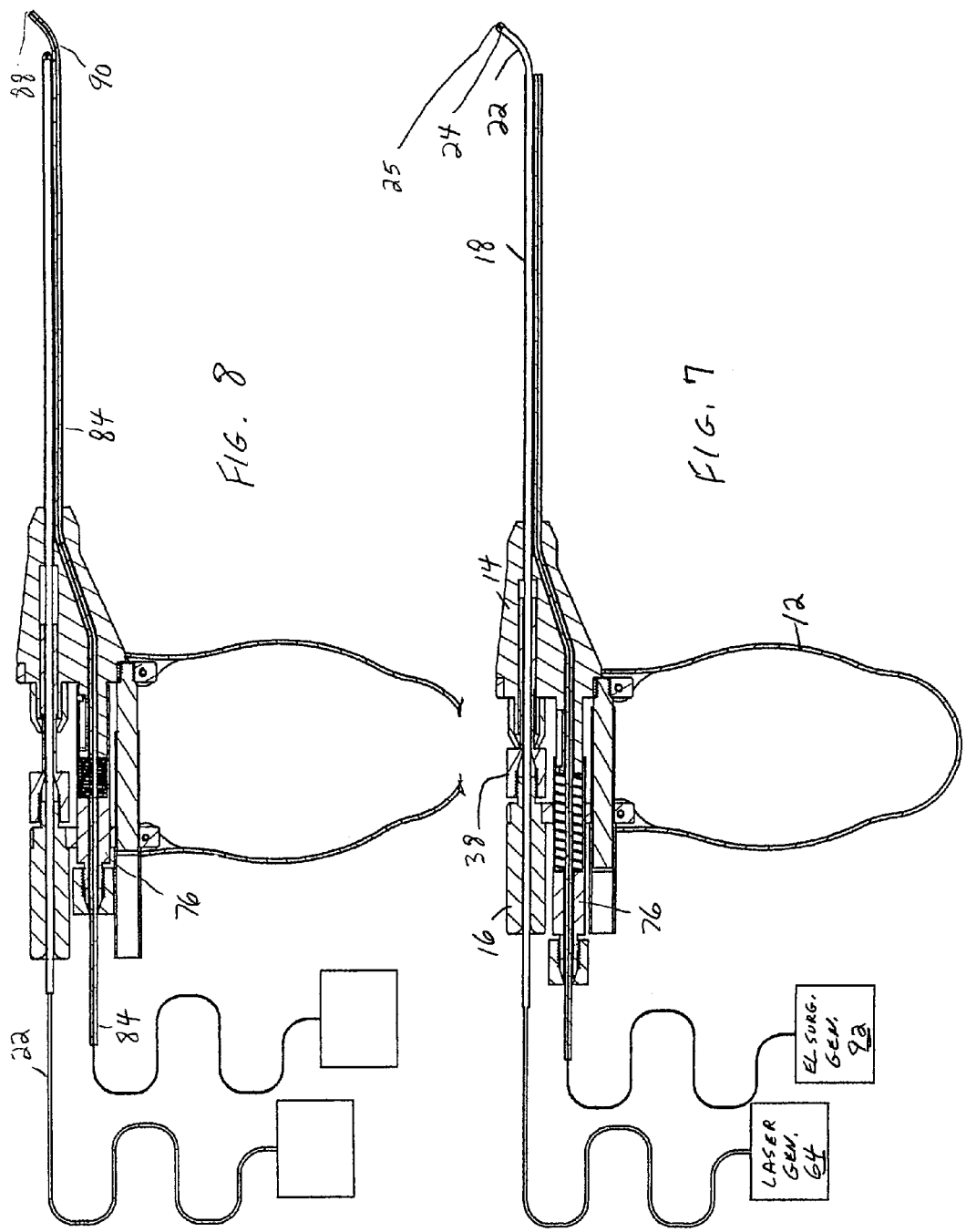

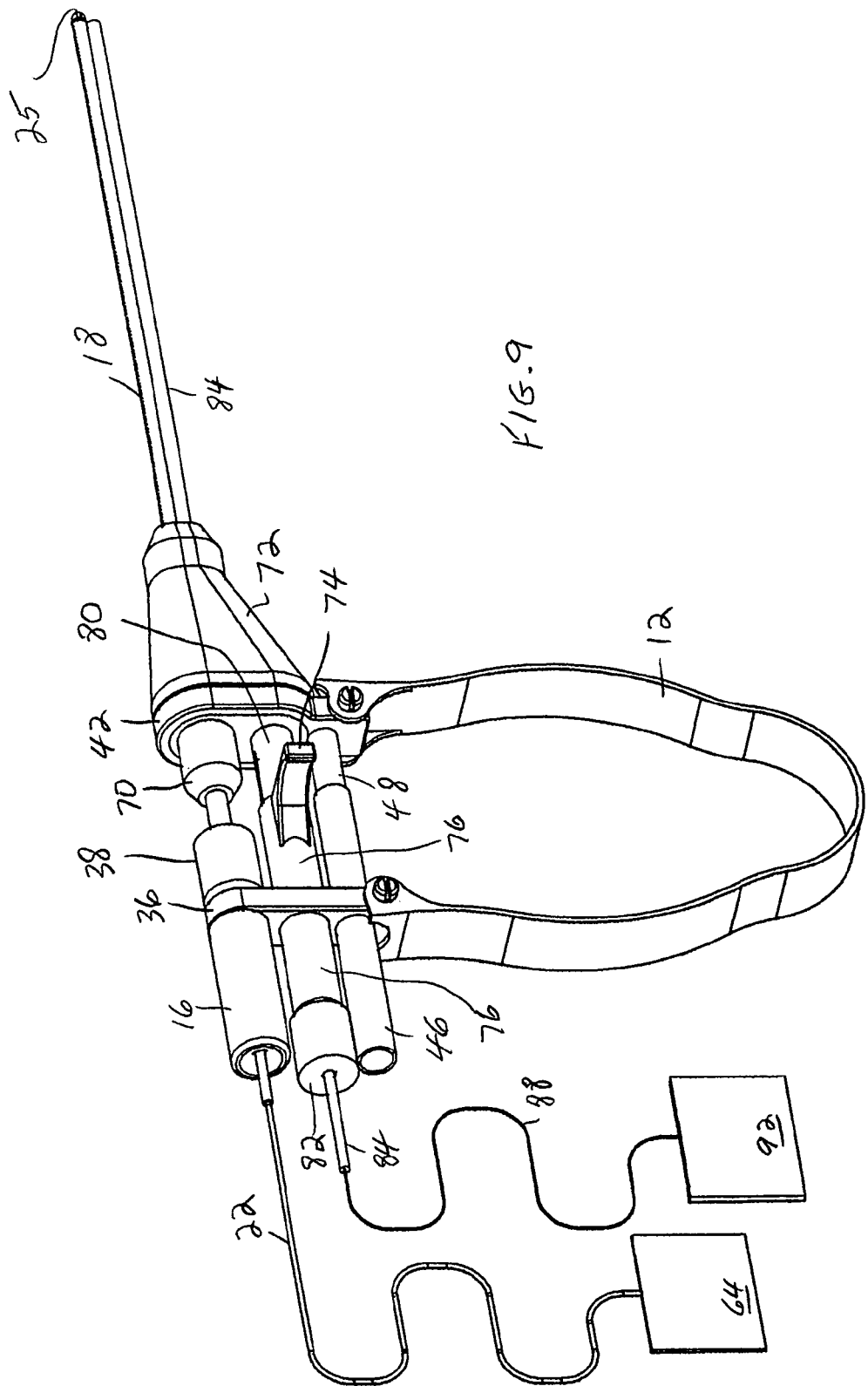

POSITION-CONTROLLABLE LASER SURGICAL INSTRUMENT

RELATED APPLICATION

A commonly-owned patent application Ser. No. 10/866,630, filed Jun. 14, 2004 DISPOSABLE ELECTROSURGICAL HANDPIECE FOR TREATING TISSUE now U.S. Pat. No. 7,101,370.

This invention relates to a laser surgical instrument in which the end of the active fiber or other beam transmitting device from which the laser beam radiation source emanates is positionable by the surgeon.

BACKGROUND OF THE INVENTION

Our prior U.S. Pat. No. 6,231,571, describes a novel electrosurgical handpiece for treating tissue in a surgical procedure commonly known as minimally invasive surgery (MIS). Among the features described and claimed in the prior application is an electrosurgical handpiece that can be used in MIS and reduces the danger of excessive heat causing possible patient harm. This is achieved in one embodiment by an electrosurgical handpiece that is bipolar in operation and that is configured for use in MIS. The bipolar operation confines the electrosurgical currents to a small active region between the active ends of the bipolar electrode and thus reduces the possibility that excessive heat will be developed that can damage patient tissue. Moreover, the position of the active region can be controlled to avoid patient tissue that may be more sensitive to excessive heat. Preferably, the handpiece is provided with a dual compartment insulated elongated tube, each of the compartments serving to house one of the two wires of the bipolar electrodes. The electrode for MIS use is preferably constructed with a flexible end controllable by the surgeon so as to allow the surgeon to manipulate the end as desired during the surgical procedure. In a preferred embodiment, the flexible end is achieved by weakening at the end the housing for the electrode, and providing a pull string or wire connected to the weakened housing end and with a mechanism at the opposite end for the surgeon to pull the string or wire to flex the housing end to the desired position. This feature allows the surgeon to position the active electrode end at the optimum location for treating, say, a herniated disk to remove undesired regions and to provide controlled heat to shrink the tissue during surgery. In FIGS. 3–7 of the prior application, a suitable bipolar electrode is described, which comprises a pair of rounded electrodes with spaced flat sides separated by an insulating layer. FIGS. 8–10 illustrate a suitable unipolar electrode construction of the flexible end handpiece. FIG. 12 illustrates how such an electrode can be used for the reduction of herniated disks in a laparoscopic procedure. FIG. 19 shows a construction that combines both a bipolar and a unipolar electrode either of which can be selected by the surgeon for use with the procedure. FIG. 20 shows a scissors end that can be constructed as a bipolar electrode for certain purposes. Other constructions to provide easier flexing of the handpiece end, as well as the use of memory metals to control the position of the extended electrode, are also discussed.

One limitation of the handpiece constructions described in these prior applications is the relatively high fabrication costs, which deters single uses of the handpiece by the surgeon.

Nowadays, surgeons prefer if feasible disposable instruments that can be discarded after one use and no longer need sterilization and sterile packaging for future uses.

The referenced co-pending patent application describes a relatively inexpensive handpiece construction for such instruments with flexible tips. Thus, the handpiece can be made so as to be disposable if so desired.

The present application is concerned with surgical lasers, constructed in the form of a gun for MIS procedures. A drawback of known constructions is that the active laser tip from which the laser radiation beam emanates is typically in a fixed position, or in some more modern versions can be extended forward but typically only in a straight line. This can present problems for the surgeon user as it may not be easy to reach with the laser beam surgical sites located behind other tissues or not positioned in-line with the typical cannula through which the laser fiber is introduced into the patient's tissue.

SUMMARY OF THE INVENTION

The present invention hereby incorporates by reference the total contents of the co-pending prior application Ser. No. 10/866,630 and U.S. Pat. No. 6,231,571. The present invention describes and claims among other things a handpiece construction for a laser probe instrument with a position-controllable tip. Since the present application otherwise makes use of some of the same teachings of the prior application and patent, it was felt unnecessary to repeat in the body of this specification many of the details present in the contents of the prior application and patent. The present description will be confined solely to the modifications in the handpiece construction that allow for construction of a laser probe with a position-controllable active tip. A further feature is an inexpensive construction that allows for disposability if desired. Another feature is a laser probe with a position-controllable tip combined with an electrosurgical electrode also with a position-controllable end whereby the operating surgeon can use with the same handpiece either surgical mode if desired during a particular surgical procedure. More specifically, the construction of the present invention that incorporates an electrosurgical electrode can provide both bipolar and unipolar operation separately or in the same handpiece, and can use the same constructions described in the prior application and patent for providing the extendable and retractable straight and/or curved active electrode tips, as well as many of the details for providing a flexible end or a straight end with a curved extendable electrode, including use in the various medical procedures described in the prior applications and known to others in this art in which electrosurgical currents are used to modulate patient tissue, meaning to cut, ablate, shrink, and/or coagulate tissue. For more details, the reader is directed to the prior application, the referenced patent, and to the following publications dealing with laser surgery, all of which are hereby incorporated by reference:

1. The Practice of Minimally Invasive Spinal Technique, edited by Savitz, Chiu, and Yeung, $1^{st}$ Ed., 2000, and in particular Ch. 10 directed to Percutaneous Laser Discectomy, Ch. 15 directed to Cervical Endoscopic Discectomy With Laser ThermoDiskoplasty, and Ch. 42, Endoscopic Laser Foraminoplasty.

2. Journal of Clinical Laser Medicine And Surgery, Vol. 13, No. 1, 1995, Pgs. 27–31, which describes a side firing Holmium:YAG Laser fiber intended to reach sites not easily reached by an in-line needle fiber.

3. Surgical Application Of Lasers, by Dixon, Year Book Medical Publishers, 1983.

4. $CO_2$ Laser Surgery, By Kaplan and Giler, Springer-Verlag, 1984.

5. Endoscopic Laser Surgery of the Upper Aerodigestive Tract, by Steiner and Ambrosch, Thieme Stuttgart, 2000.

The handpiece constructions of the present improvement are focused for the most part at the gun or handle end of the handpiece, meaning the part of the handpiece held in the hand of the surgeon and operable by the surgeon to extend and retract the active fiber tip. It will be understood that any and all kinds of beam-generating lasers can be connected to the novel handpiece construction of the invention by means of conventional optical fibers, unimode or multimode, or by means of thin transmission probes. The thin optical fibers that are typically soft and flexible, in the preferred embodiment, can be directly incorporated permanently or removably in the novel handpiece construction of the invention, essentially in a similar manner to that of the electrosurgical electrode in the copending application. Moreover, any and all kinds of laser fibers of various sizes and lengths appropriate for the surgical procedure contemplated can be employed. Hence, the present description will focus on the gun construction which accommodates the active fiber, and the means for extending and retracting the active fiber end, and the construction that allows the fiber to be combined with an electrosurgical electrode for greater versatility.

In a preferred embodiment according to the invention, the handle end of the handpiece is constructed preferably of known plastics, such as ABS, and thus can be, for example, molded in several parts and simply assembled by being force-fitted and/or adhered together by suitable adhesives, or snapped together as is well known in the art for assembling plastic members. Preferably, all parts of the handle end apart from some metal parts, optionally a metal spring, and the electrode assembly if included can be made of inexpensive plastic.

In accordance with another preferred embodiment, the fiber tip position is controlled by associating it with a wire, tube, or other elongated member constituted of known shaped memory material, typically metal but can also be of well known plastics. The elongated member constituted of shaped memory material is preset or pre-configured to a specific configuration and then mounted into a tubular support member in its retracted position. When the fiber with its associated shaped memory member is extended, the shaped memory member assumes its preset configuration forcing the flexible fiber to which it is connected or which houses it to also assume the same configuration. In a further preferred embodiment, the tubular support member is straight, and the shaped memory member is pre-curved, so that the extended soft flexible fiber assumes the same curvature when extended from the tubular support member.

In a further preferred embodiment, the handle is a one-piece member connected across slidable body parts configured such that squeezing of the handle by the surgeon causes the body parts to come together which action causes the active end of the fiber to extend out of the tubular support member.

In accordance with still another preferred embodiment, the handpiece combines with the position-controllable optical fiber an electrosurgical electrode, also extendable into a controlled position, with either the optical fiber or the electrode being selectively extendable by the user. Each of the optical fiber or the electrode are connected respectively to laser beam generating apparatus and to an electrosurgical current generator, and thus either of the two instruments can be selected and operated by the surgeon from the same handpiece during the same or different procedures.

The constructions of the invention will provide the same important benefits as obtained with other surgical laser and electrosurgical devices not only for MIS of herniated disks but also for other MIS procedures where controlled tip position and/or controlled heat generation is of importance as described in the prior applications and publications, as well as for general surgical procedures where volumetric reduction of tissue is desirable.

While the invention of the handpiece of the invention has focused on low-cost fabrication allowing disposability or one-time use, it will be understood by those skilled in this art that the same handpiece can also be reusable if the practitioner so desires, by appropriate sterilization after each use. Most forms of sterilization can be used by an appropriate choice of handpiece materials, such as high-temperature plastics, but gas sterilization as is well known in this art can also be used if heat-sensitive material may be present.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals designating the same or similarly functioning parts.

BRIEF DESCRIPTION OF THE DRAWINGS

In the drawings:

FIG. 4 is an enlarged view of the working end of the surgical laser handpiece illustrated in FIG. 3;

FIG. 4A shows a variation in which the memory metal is in the form of a strip;

FIG. 5 is an exploded view of the surgical laser handpiece of FIG. 1;

FIG. 7 is a vertical cross-sectional view of the surgical handpiece of FIG. 6 but with the working end with the optical fiber extended into operating position;

FIG. 8 is a vertical cross-sectional view of the surgical handpiece of FIG. 1 but with the working end with the electrosurgical electrode extended into operating position;

FIG. 9 is a perspective view of the surgical handpiece of FIG. 6.

DETAILED DESCRIPTION OF THE PREFERRED EMBODIMENTS

The reader is directed to the referenced prior application and patent for a more detailed description of the prior applications which will assist in understanding the improvements offered by the present application.

In the present application, the handpiece configuration remains essentially similar to the prior configurations. It can comprise the use of a pulling wire to flex a flexible end of an outer tube housing for the handpiece while simultaneously extending the fiber or electrode from the end of the outer tube. Or, preferably, the outer tube end is not flexible, but the fiber or electrode distal end is constituted of memory metal or has been given a pre-bent contour such that, when extended from its outer tube housing, it assumes a preset curved or straight position that allows the surgeon to reach with the active end of the electrode patient sites behind, say, other tissues more easily. Other electrode constructions that allow the surgeon to extend an active electrode end from a surgical elongated tubular member and cause the active end to assume straight or curved configurations can also be alternative constructions in accordance with the present invention. When both a laser fiber and electrosurgical electrode are combined, preferably a dual compartment tubular housing is employed, with one of the compartments housing the laser fiber with associated shaped memory member, and the other compartment housing the electrosurgical electrode. Or, alternatively, side-by-side separate tubular members can be provided for each.

Figure 1:
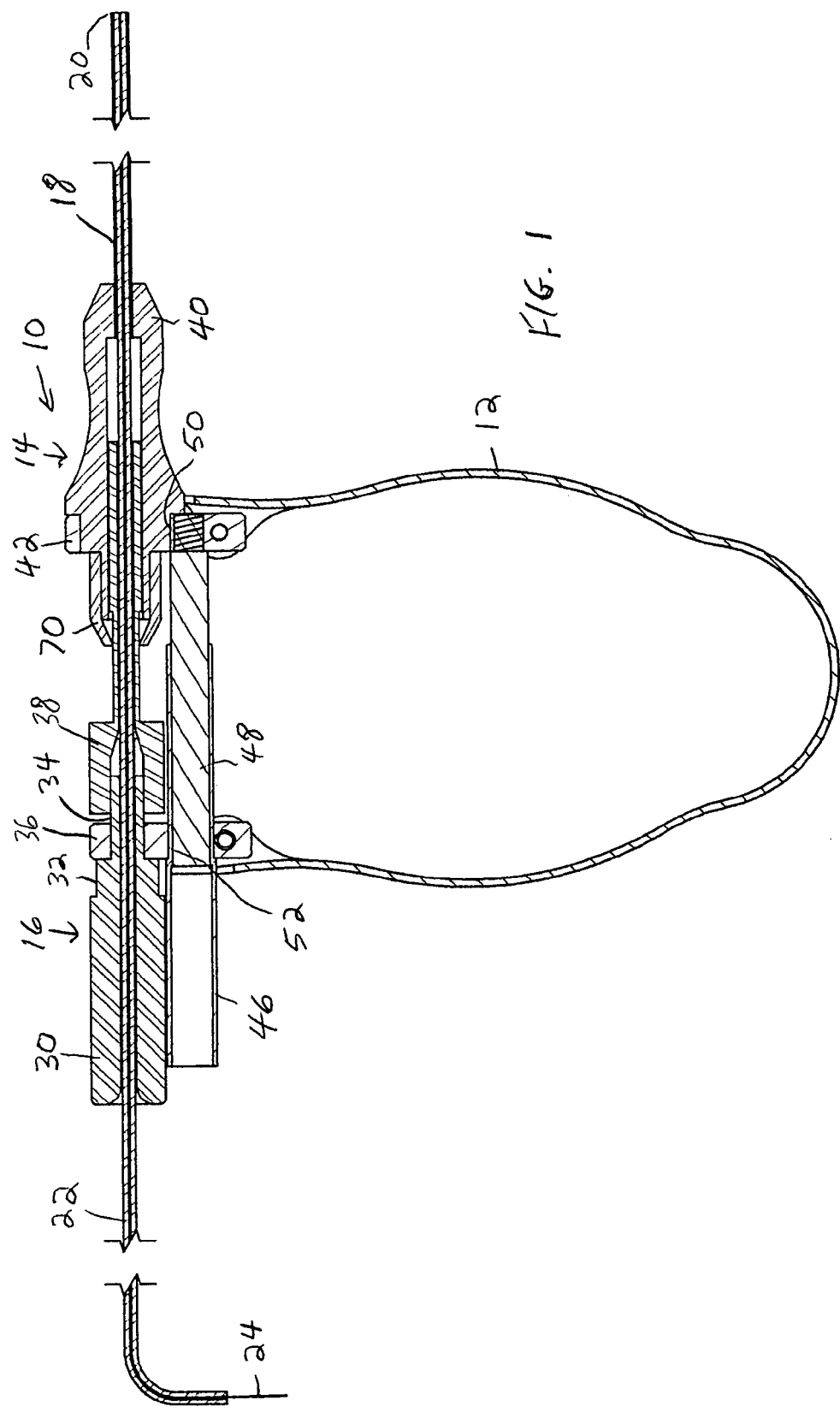
FIG. 1 is a vertical cross-sectional view of one form of surgical laser handpiece in accordance with the invention with the working end shown in its retracted position.
Figure 2:
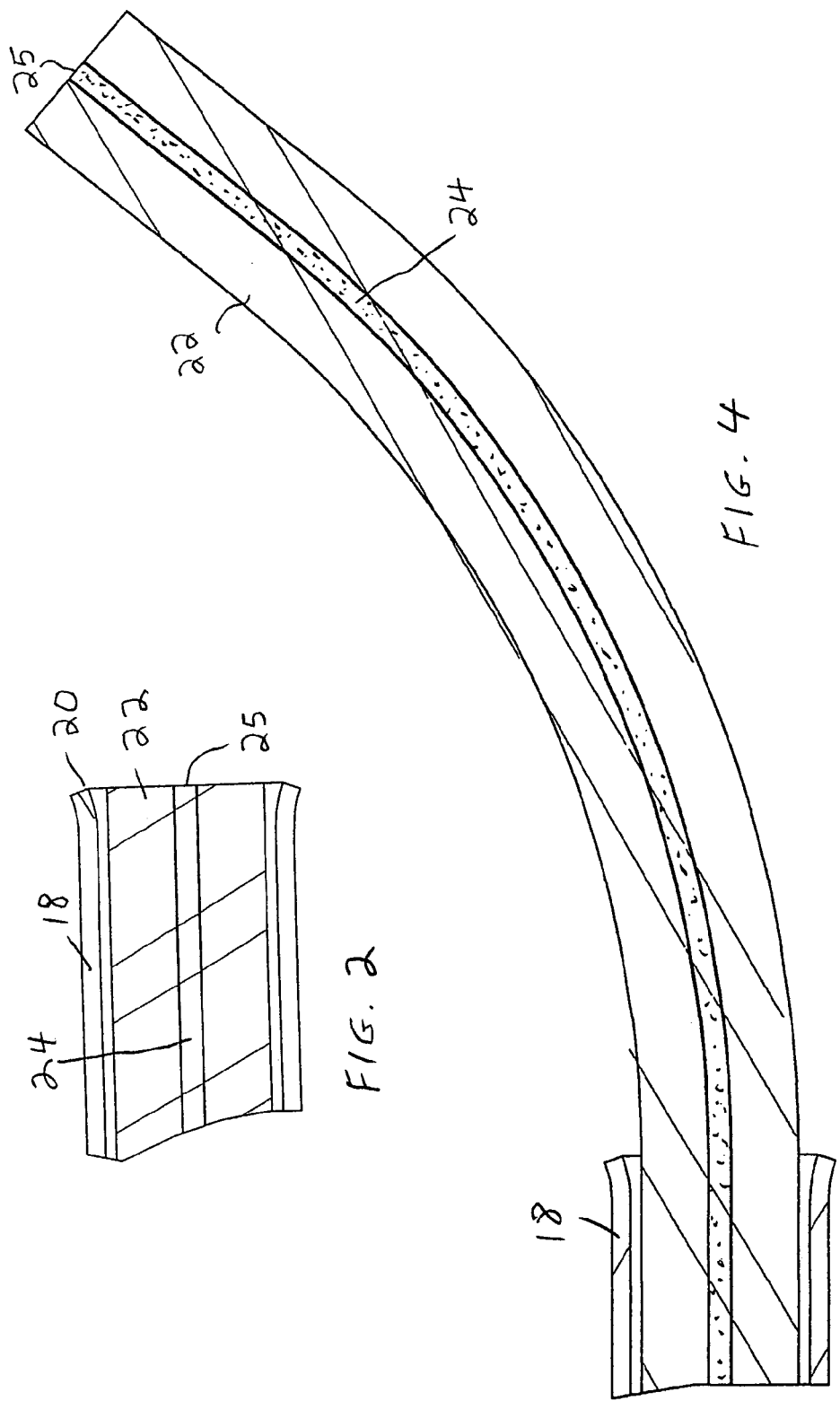
FIG. 2 is an enlarged view of the working end of the surgical laser handpiece illustrated in FIG. 1.
Figure 3:
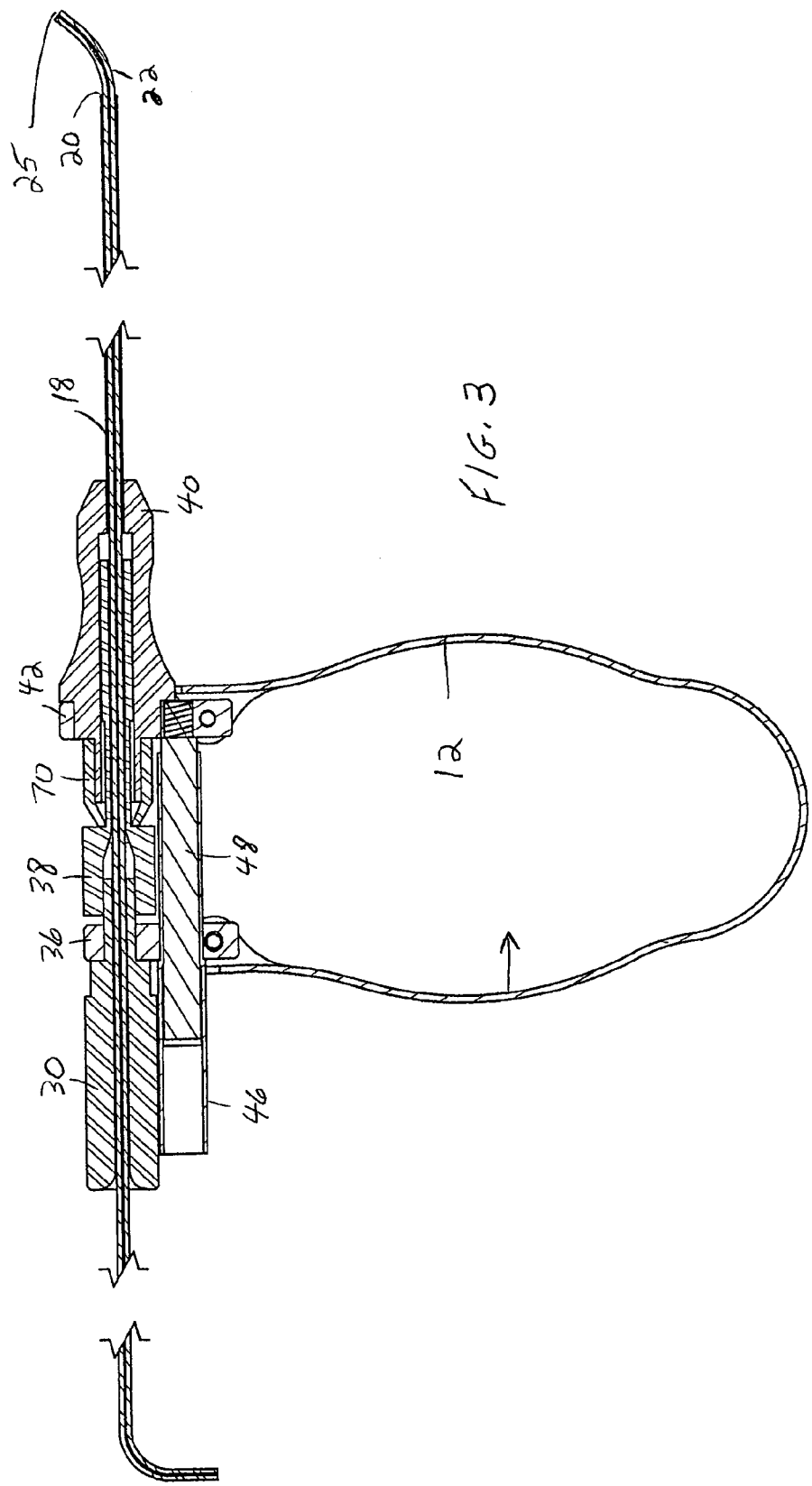
FIG. 3 is a vertical cross-sectional view of the surgical laser handpiece of FIG. 1 but with the working end with the optical fiber extended into operating position.

FIG. 1 shows one form of handpiece 10 for use with one form of a laser surgical instrument of the invention. It comprises a squeezable handle 12 of elastic material connected to and across front 14 and rear 16 main slideable body parts with the front body part 14 enclosing an elongated outer tubular housing 18 from whose distal end 20 (FIG. 2) an elongated inner tube 22 constituted of shaped memory material in turn housing a typical optical fiber 24 whose active tip 25 from which the radiation beam emanates can be extended and retracted when the handle 12 is squeezed or released, respectively. The rear body part 16 comprises a generally cylindrical member 30 with a middle reduced diameter section 32 and a distal reduced diameter threaded section 34. One of two handle mounts 36 is threaded onto the distal section 34. The distal section 34 at its right end is slotted and forms with a threaded collet 38 a releasable lock for the active fiber. The front body part 14 comprises a nosepiece 40 on which is mounted the second handle mount 42. Those two handle mounts, as will be evident from the exploded view of FIG. 5, are mounted by way of screws 44 to the handle 12. Mounted below the body parts are a tubular slide support 46 which slides over a screw 48 whose right end is threaded and screwed into a threaded hole 50 in the second handle mount 42 after passing through an enlarged bore 52 in the first handle mount 36. As the handle 12 is squeezed, the tubular slide support 46 carrying the rear body part 16, driven by the slideable left handle mount 36, slides to the right in FIG. 1 over the screw 48 connected to the right handle mount 42. This construction, of relatively low cost, provides a smooth stable sliding action.

Figure 6:
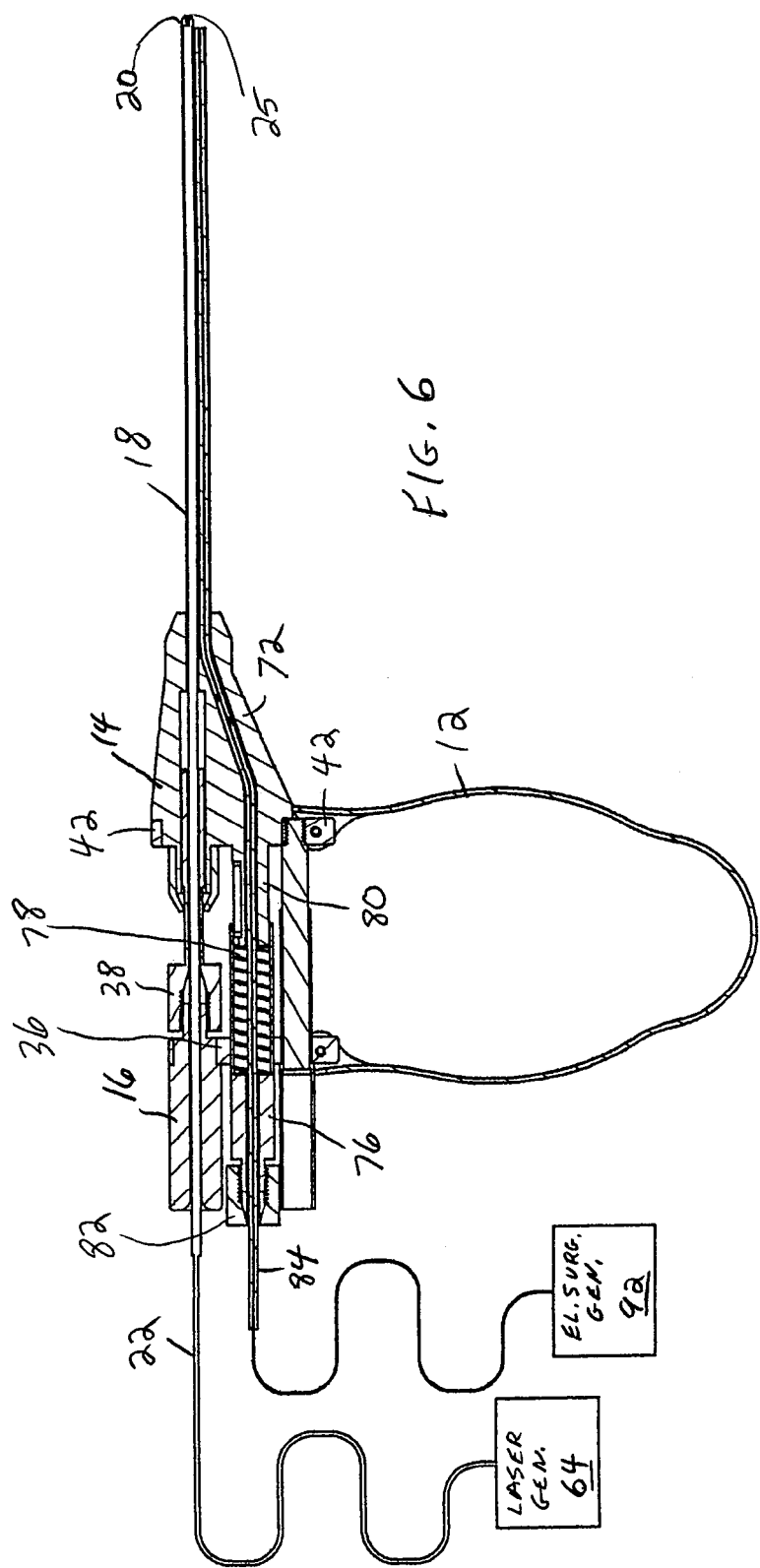
FIG. 6 is a side view of one form of surgical handpiece in accordance with the invention combining a laser with an electrosurgical electrode.

At the distal end of the assembly 10, the outer tube 18, for example, of metal or stiff plastic, is mounted as by a suitable adhesive into a front bore of the nosepiece 40 and extends forwardly a considerable distance, for example, about 12–20 inches. Slidable within that outer tube 18 is a thin tube 22 (FIG. 5) of memory material enclosing a standard optical fiber 24 (not shown in FIG. 5). One example of a shaped memory material, which is not to be deemed limiting, is NITINOL, a nickel-titanium alloy. The memory tube 22 extends through the nosepiece 40, through the collet 38 and rear cylindrical member 30 and exits the assembly at the left rear. From its termination extends the fiber 24 which ultimately can be connected to a conventional laser system which, as an example, may be a HO-YAG laser source beam generator 64 (FIG. 6). With the collet 38 loosened, the entire tube 22 of memory material and its inner fiber 24 can be removed from the left back end of the assembly 10. When the collet 38 is tightened, the slitted end 34 grips the tube 22 of memory material and its inner fiber and the latter is fixed to the rear body part 16. As will be evident from this description, when the handle 12 is squeezed, the rear body part 16 moves to the right pushing and extending the tube 22 of memory material and its inner fiber 24 out of the distal end 20 of the outer tube 18. This action is illustrated in FIG. 4. Typically, as explained earlier, the tube 18 of the gun is preferably straight but the tube 22 of memory material has been pre-configured to assume a curved position. Thus, when the tube 22 of memory material and its inner fiber 24 are extended, the tube 22 curves upward as shown in FIG. 4 and forces the very flexible inner fiber 24 to assume the same curved shape. FIG. 4 is an enlarged view showing this action. When the handle is released, the biasing force exerted by its elastic nature causes the two handle halves to separate retracting the tube 22 of memory material and its inner fiber 24 back within the stiff outer tube 18 which forces the tube 22 of memory material into a straight position. The exploded view of FIG. 5 illustrates how the various parts can be assembled to form the completed handpiece 10 of FIG. 1.

The invention is not limited to enclosing the flexible fiber in a tube of memory material. The latter can be replaced by a strip of memory material to which the fiber is attached so it is forced to adopt the shape assumed by the memory strip. This variation is shown in enlarged form in FIG. 4A with the memory strip shown at 66 and the fiber at 68.

In FIG. 1, a sleeve 70 is mounted on the front body part 14 and merely serves to keep the interior clean if exposed to liquid or other debris. Loosening of the collet 38 allows the laser fiber to be removed from the handpiece and replaced by another fiber if desired.

If desired, the resilient handle 12 can be replaced by a flexible handle supplied with a resilent band as described in the copending application, or by some other equivalent construction providing a biasing force. In the embodiment shown, the collet 38 can be permanently secured to the rear body part 16 so that the fiber is not changeable, but the preferred handpiece construction of the invention allows for a changeable memory member with a different fiber if desired.

The assembly can be made permanent by force-fitting together of the parts or by using adhesives between the assembled parts. A preferred way is to slightly taper the various parts that telescope together of a suitable plastic, apply as by brushing to the eternal surface of the inner fitting part a suitable solvent for the plastic, and force the parts together. The solvent slightly dissolves a thin surface layer of the plastic and when the solvent evaporates, the two contacted parts are essentially fused together permanently. For a removable fiber, the fiber with its memory member can be added later and configured so that it moves freely inside the aligned bores. With a screwed nose piece, the fiber can be locked into place for use. Or if the fiber is to be made a permanent part of the handpiece, then it can be provided with an enlarged stop at its internal terminating end to prevent inadvertent removal.

Once the surgeon has positioned the tubular working end of the handpiece inside the typical cannula with respect to the tissue to be operated on, he or she then activates the laser apparatus causing emission of a laser beam from the active tip capable of causing ablation, shrinkage, or excision of tissue, or cauterization of a blood vessel in the usual way. Other usable mechanical or electrical structures following the teachings of the prior applications will be appreciated by those skilled in this art. As with the embodiments of the prior application, the tube 18 can be insulating if desired.

In all embodiments, the tubular housing 18 can be plastic, such as ABS or DELRIN, or of insulated relatively stiff metal that will not bend except where desired. For example, the tube outside diameter can be typically about 0.04–0.1 inches. For the application of shrinking herniated tissue via a cannula, the tubular housing is typically about 15–20 inches long. It will also be noted that the features set forth in commonly owned U.S. Pat. Nos. 6,652,514 and 6,712,813, namely incorporating the handpiece with the flexible tip of the invention into the intelligent operating-mode selection system of the earlier patent, and/or as a procedure-dedicated handpiece of the later patent, can also be readily implemented by those skilled in this art following the teachings of those patents.

The automatic retraction of the fiber may be caused by an internal compression spring. Alternatively, the plastic handle can be configured such that it has built-in resilience which tends to return it to its open position as shown in FIG. 1 in the preferred embodiment. As a further alternative, a resilient leaf or helical spring, for example, of metal or fiberglass, can be fitted inside of or between the handle sides to provide an outward bias force tending to maintain the handle sides in their open position. However, it is preferred that the handle itself be electrically-insulating to prevent any chance of an electric shock to the surgeon or the patient if an electrosurgical electrode is added.

An important advantage of the construction described is its inexpensive construction and fabrication thus allowing handpiece disposability after one use. However, as explained above, the handpiece of the invention can also be reused if desired by appropriate sterilization after each use. A further advantage with the use of an elongated tubular member constituted of shaped memory material is that the latter also serves a protective function of the fiber end when extended.

In the preferred embodiment, the position of the active laser end is controlled by housing the flexible fiber in an elongated tubular member constituted of a known shaped memory material, and thus when the shaped memory metal tube is extended, it assumes its pre-configured shape thereby forcing the flexible fiber inside of it to assume the same shape. Alternatively, the elongated member constituted of shaped memory material can be formed by a wire or strip that is attached along its length, at least where it is extended and retracted from the outer tube, to the fiber. Again, the same result is obtained as with the tubular inner member as the preset wire when freed from the outer tube assumes its memorized curved shape and forces the fiber to follow. It will also be appreciated that rotation of the handpiece will cause the extended fiber tip to trace a circle allowing access to various possible surgical sites from the same positioned cannula or working channel of an endoscope. While the preferred embodiment employs a fiber whose radiation beam is in-line with the axis of the fiber, it is of course possible to bevel the fiber end so that the radiation beam exits laterally to the fiber axis to produce the so-called side-firing tips. While the preferred embodiment shows a straight outer tube in which the extended fiber assumes a curved shape, it is also possible for the extended fiber to extend in-line with the outer tube axis if so desired, or that the end of the outer tube is curved and the extended fiber extends in-line from the curved outer tube or provides additional or different curvature from the outer tube. It is also possible following the teachings herein disclosed for the outer tube to have a bayonet shape. The bayonet shape, as is known in other contexts, provides improved surgeon visibility of the active laser tip at the surgical site.

It will also be evident to those skilled in this art that an ON-OFF switch can be added to the handpiece and wires provided to send a control signal back to the laser system unit to turn the laser generator on or off under control of the surgeon operating the switches on the handpiece. Further, our U.S. Pat. Nos. 6,652,514 and 6,712,813 describe, respectively, an intelligent selection system for an electrosurgical instrument and a procedure-dedicated electrosurgical handpiece, the contents of which are hereby incorporated by reference. In the former, fingerswitches are added to the handpiece and impedances such that when a fingerswitch is activated, a control signal current determined by the impedance is transmitted back to the electrosurgical unit, which, as one example, incorporates a microcontroller and a suitable memory or computer routines that are selected by the incoming control signal current and thus sets in the electrosurgical unit the operating electrosurgical mode and if desired operating conditions such as power level and on-time duration that are specific to the procedure that the surgeon intends to carry out. The latter adds to the former the teaching of a handpiece incorporating a specific impedance and also provided with an integral electrode dedicated to a particular procedure. These teachings are easily incorporated in the laser instrument of the present invention. For example, one or more fingerswitches can be added to the handpiece and a suitable impedance incorporated such that, activation of a handpiece fingerswitch generates a control signal that sets an operating mode of the laser system unit, such as the laser pulse mode (single or multi-pulse), in a similar manner to that described in these referenced patents.

One of the features of the present invention is that the handpiece of the invention can easily be modified to incorporate an electrosurgical electrode into a handpiece containing a laser fiber. This is in part based on the teachings of U.S. Pat. No. 6,231,571, herein incorporated, and in particular, FIGS. 13–19. In those figures of the patent, embodiments are described that incorporate both a unipolar and a bipolar electrosurgical electrode into the same handpiece, either of which can be selectively extended by the user-surgeon during a surgical procedure. In that embodiment, squeezing the handle extends the bipolar electrode from its tubular housing, as the extension mechanism is similar to that described in connection with the other embodiments. When a unipolar electrode is to be selected, an auxiliary extension mechanism involving a slide on the side of the outer tube can be activated by the user's thumb. The slide is connected to the unipolar electrode, which then is extended forwardly into operating position. It is also obvious that the operation can be reversed, with the handle operatively connected to the unipolar electrode and the slide operatively connected to the bipolar electrode. A similar principle can be employed to combine in the same handpiece a laser and an electrosurgical electrode or a laser with both a unipolar and a bipolar electrode as illustrated in FIGS. 6–8.

FIGS. 6–9 show one form of construction suitable for a multi-function (laser surgery and electrosurgery) surgical handpiece in accordance with the invention. In this preferred embodiment, a dual-compartment structure is employed. If a laser fiber with a single electrosurgical electrode only is incorporated, then only a two-side-by-side compartment structure is needed; if in addition a second electrosurgical electrode is incorporated, then a third compartment would be required. In its simplest form, the handle could be operatively connected to operate, by means of the handle, say, the laser fiber in a first compartment, a first slide on one side would be operatively connected to operate, say, the bipolar electrode in a second compartment, and a second slide on the opposite side would be operatively connected to operate, say, the unipolar electrode in a third compartment. The active components can be rearranged so that the different modalities are otherwise arranged. Preferably, the fiber connections and electrical connections are made at the rear as illustrated in FIG. 6. However, it is also possible to bring in the laser connection from the rear and the electrical connections from the side, as it may be simpler to bring in the electrical wires for the electrode(s) from the side.

A preferred embodiment is illustrated in FIG. 6, wherein the construction and operating mechanism for extending and retracting the laser fiber is the same as in FIG. 1 (the same reference numerals are thus used). Thus, the handpiece comprises a squeezable handle 12 connected to and across front 14 and rear 16 main relatively slideable body parts enclosing an elongated outer tubular housing 18 from whose distal end 20 an elongated inner tube constituted of shaped memory material 22 in turn housing a typical optical fiber 24 whose active tip 25 from which the radiation beam emanates can be extended and retracted when the handle 12 is squeezed or released, respectively. At the left end a adjustable collet 38 mounted on the rear body part 16 and when tightened locks the memory tube and flexible optical fiber to its outer tube housing 18. The exiting fiber at the left end can be ultimately connected to a conventional laser system which, as an example, may be a HO-YAG laser source 64.

The outer 18 and inner 22 tubular members for the fiber 24 can be as shown as a separate tubular system, or alternatively occupy one compartment of a multi-compartmented exterior tubular member similar to the constructions shown in the referenced patents. The front body part 14 is fixed, and the rear main body part 16 is connected to the inner tube 22.

A separate structure is provided for the electrosurgical electrode. It includes a bottom part 72 of the enlarged front body part 14, a slide 74 (not shown in FIG. 6 but shown in FIG. 9) is connected to the outside of a slideable cylinder 76 having an internal bore containing a compression spring 78. The cylinder 76 slides on a rearwardly projecting part 80 of the fixed part 72. A rotatable collet 82 mounted at the rear of the cylinder 76, when tightened in the usual way, grips a tube 84 housing an inner tube 86 containing a unipolar electrosurgical electrode 88 inside a tube 90 of memory metal. The electrosurgical electrode may be a unipolar or bipolar electrode. Alternatively, still another tubular member can be added to the assembly for housing the other of the unipolar or bipolar electrodes, and the latter in turn activated by a second slide connected to the added electrode.

The slide mechanism is operated by the thumb of the surgeon moving the slide 74 to the right of FIG. 9. This causes the cylinder 76 to move to the right against the bias of the spring 78 and causes the gripped tube 90 and electrode 88 to be extended from the outer tubular member 84, and the electrode will assume the pre-set shape of the memory tube 90, as shown in FIG. 8. When the thumb pressure is released, the spring forces the cylinder 76 back to its rear starting position and causes the electrode to retract. A second slide mechanism if provided can be constructed on the same principles as the first slide to operate in the same way. Separate energizing conducting wires for the two electrodes can be provided extending out from the rear or sides of the multi-compartmented housing. The wires, which are typically flexible, where connected to their respective electrodes, can be provided with some slack so that extension of an electrode, which typically only extends about 1–2 inches, will not cause undue strain on the wire itself. If desired the use of strain-relief wire mounts can be added. Such multimodality handpieces can be used in procedures where a cannula in unnecessary, or with a somewhat larger cannula to house a larger multi-compartmented exterior tubular member.

FIG. 7 shows the instrument of FIG. 9 with the handle squeezed to extend the fiber, whereas FIG. 8 shows the instrument of FIG. 9 with the slide actuated to extend the electrosurgical electrode.

As in the earlier applications for the electrosurgical handpiece, two electrically-insulated wires are needed for the bipolar electrode, but for a unipolar handpiece, only a single wire may be necessary connected to a typical unipolar electrode such as a ball, point, rod, or loop, as examples. The means for making contact between the wire ends and the electrosurgical electrode can be the same means described in the copending patent application. The electrode where it exits from the assembly can be connected in the usual way to conventional electrosurgical apparatus, an example of which is given in the referenced patent and application.

As in the previous applications directed to electrosurgery, it is preferred that for the embodiment containing the electrosurgical electrode, the electrosurgical currents be in the MHz range, preferably 34 MHz, sometimes referred to as radio frequency electrosurgery, as it is found that best results are obtained with this range of electrosurgical currents.

As used herein, by "axial" is meant parallel to the long axis of the fiber or electrode (horizontal in FIGS. 1 and 6). By "lateral" is meant transverse to the long axis of the fiber or electrode.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A surgical laser handpiece comprising:
   (a) an elongated tubular first member having a first end and a distal second end,
   (b) an active flexible laser fiber having an active tip from which a laser beam may emanate,
   (c) position-controlling means within the tubular first member and connected to and associated with the laser fiber for controlling the position of the active tip when the laser fiber together with the position-controlling means is extended from the tubular first member,
   (d) means operatively connected to the position-controlling means for sliding the position-controlling means under the control of a user such that the active tip of the laser fiber can be selectively extended and retracted from the tubular first member,
   (e) the position-controlling means comprising a pre-configured member constituted of shaped memory material and connected to and extendable with the laser fiber such that the active tip of the extended laser fiber follows the pre-configured shape of the pre-configured member.

2. A surgical laser handpiece as set forth in claim 1, wherein the position-controlling means comprises a second tubular member slidable within the tubular first member, the laser fiber being positioned within the second tubular member.

3. A surgical laser handpiece as set forth in claim 1, wherein the position-controlling means comprises a strip-shaped member slidable within the tubular first member, the laser fiber being positioned adjacent to and attached to the strip-shaped member.

4. A surgical laser handpiece comprising:
(a) a first main body,
(b) a second main body slidingly coupled to the first main body,
(c) a squeezable handle connected to and across the first and second main bodies such that, when the handle is unsqueezed, the first and second main bodies assume a first position relative to one another, and when the handle is squeezed, the first and second main bodies assume a second position relative to one another,
(d) biasing means for biasing the first and second main bodies into their first position,
(e) an elongated first tubular member having a first end and a distal second end,
(f) an active laser fiber slidingly mounted within the first tubular member and extendable from the distal second end of the first tubular member and connected to one of the first and second main bodies, the laser fiber having a radiation-receiving end and at least one active tip adjacent the distal second end of the first tubular member and from which a laser beam can emanate when the fiber is activated,
(g) position-controlling means associated with the laser fiber for controlling the position of the active tip when the latter is extended from the first tubular member,
(h) whereby, when the fiber is activated and the handle squeezed, the first and second main bodies assume their second position and the active tip of the fiber is extended out of the distal second end of the first tubular member and is forced to assume a position determined by the position-controlling means.

5. A surgical laser handpiece as set forth in claim 4, wherein the position-controlling means comprises a pre-configured member constituted of shaped memory material and connected to and extendable with the fiber.

6. A surgical laser handpiece as set forth in claim 5, wherein the first tubular member is straight, the fiber is soft and flexible, and the member constituted of shaped memory material has a pre-configured curved shape when extended out of the first tubular member.

7. A surgical laser handpiece as set forth in claim 5, wherein the position-controlling means comprises a second tubular member constituted of the shaped memory material and connected to said one of the first and second main bodies and slidable within the first tubular member, the fiber being positioned within the second tubular member and being connected to and slidable with the second tubular member within the first tubular member.

8. A surgical laser handpiece comprising:
(a) an elongated first tubular member having a first end and a distal second end,
(b) an active flexible laser fiber having an active tip from which a laser beam may emanate,
(c) position-controlling means within the first tubular member and connected to the laser fiber for controlling the position of the active tip when the laser fiber is extended from the tubular first member, the position-controlling means comprising a second tubular member slidable within the first tubular member, the laser fiber being positioned within the second tubular member,
(d) means operatively connected to the position-controlling means for sliding the position-controlling means under the control of a user such that the active tip of the laser fiber can be selectively extended and retracted from the first tubular member,
(e) the position-controlling means comprising a pre-configured member constituted of shaped memory material and connected to and extendable with the laser fiber, the position-controlling means further comprising a strip-shaped member slidable within the first tubular member, the laser fiber being positioned adjacent to and connected to the strip-shaped member,
(f) first and second main bodies, the first main body being connectable to the second tubular member, the second main body being connectable to the tubular first member, wherein one of the first and second main bodies being located rearwardly of the other of the main bodies
(g) further comprising a handle composed of resilient material connected between the first and second main bodies.

9. A surgical laser handpiece comprising:
(a) an elongated tubular first member having a first end and a distal second end,
(b) an active flexible laser fiber having an active tip from which a laser beam may emanate,
(c) position-controlling means within the tubular first member and connected to the laser fiber for controlling the position of the active tip when the laser fiber is extended from the tubular first member,
(d) means operatively connected to the position-controlling means for sliding the position-controlling means under the control of a user such that the active tip of the laser fiber can be selectively extended and retracted from the tubular first member,
(e) further comprising an electrosurgical electrode having an electrically active end and located alongside the laser fiber together with separate means for selectively extending and retracting the active end of the electrosurgical electrode, the electrosurgical electrode being unipolar or bipolar.

10. A surgical laser handpiece as set forth in claim 9, further comprising additional position-controlling means associated with the electrically active end of the electrosurgical electrode and operative to control the position of the electrically active end when the electrosurgical electrode is extended from the first tubular member.

11. A surgical laser handpiece as set forth in claim 9, wherein the separate means for selectively extending and retracting the active end of the electrosurgical electrode comprises a slide mounted on the side of the handpiece.

12. A surgical laser handpiece as set forth in claim 9, wherein the tubular first member comprises an exterior tubular member, the tubular first member housing the laser fiber, the exterior tubular member housing the electrosurgical electrode.

13. A surgical laser handpiece as set forth in claim 9, further comprising a laser beam generator connected to the laser fiber, and an electrosurgical current generator connected to the electrode.

* * * * *